(12) United States Patent
Yang et al.

(10) Patent No.: US 11,511,138 B2
(45) Date of Patent: Nov. 29, 2022

(54) METHOD AND APPARATUS FOR REMOVING MICROVESSELS

(71) Applicants: University of Kansas, Lawrence, KS (US); The Regents of the University of Michigan, Ann Arbor, MI (US)

(72) Inventors: Xinmai Yang, Lawrence, KS (US); Xueding Wang, Ann Arbor, MI (US); Yannis M. Paulus, Ann Arbor, MI (US)

(73) Assignee: University of Kansas, Lawrence, KS (US)

( * ) Notice: Subject to any disclaimer, the term of this patent is extended or adjusted under 35 U.S.C. 154(b) by 804 days.

(21) Appl. No.: 15/584,317

(22) Filed: May 2, 2017

(65) Prior Publication Data

US 2017/0312552 A1 Nov. 2, 2017

Related U.S. Application Data

(60) Provisional application No. 62/330,699, filed on May 2, 2016.

(51) Int. Cl.
*A61N 7/02* (2006.01)
*A61B 5/107* (2006.01)
*A61F 9/008* (2006.01)
*A61B 5/103* (2006.01)
*A61N 7/00* (2006.01)

(52) U.S. Cl.
CPC ............ *A61N 7/022* (2013.01); *A61B 5/1079* (2013.01); *A61F 9/008* (2013.01); *A61B 5/103* (2013.01); *A61N 2007/0095* (2013.01)

(58) Field of Classification Search
CPC ............ A61N 7/022; A61N 2007/0095; A61B 5/1079; A61B 5/103; A61F 9/008
See application file for complete search history.

(56) References Cited

U.S. PATENT DOCUMENTS

| | | | |
|---|---|---|---|
| 5,158,070 | A | 10/1992 | Dory |
| 5,209,221 | A | 5/1993 | Riedlinger |
| 6,391,020 | B1 | 5/2002 | Kurtz et al. |
| 8,858,471 | B2 | 10/2014 | Barthe |
| 9,039,617 | B2 | 5/2015 | Slayton et al. |
| 9,067,053 | B2 | 6/2015 | Asami et al. |

(Continued)

OTHER PUBLICATIONS

Jo, J. Photoacoustic Imaging and High Intensity Focused Ultrasound in Biomedical Applications., 2014, pp. i-100 (Year: 2014).*

(Continued)

*Primary Examiner* — Colin T. Sakamoto
*Assistant Examiner* — Patrick M Mehl
(74) *Attorney, Agent, or Firm* — Ray Quinney & Nebeker PC; Paul N. Taylor (57) ABSTRACT

A method of removing microvessels includes applying a burst of acoustic energy at a target location, applying a pulse of optical energy at the target location, and promoting cavitation at the target location. The burst of acoustic energy has a pressure below 5.0 MPa. The pulse of optical energy at the target location has a fluence less than 100 mJ/cm$^2$. At least a portion of the pulse is concurrent with the burst and the optical energy has an optical area that is overlapping with an acoustic area of the acoustic energy at the target location.

20 Claims, 9 Drawing Sheets

(56) References Cited

U.S. PATENT DOCUMENTS

| | | | |
|---|---|---|---|
| 9,192,566 B2 | 11/2015 | Soltani et al. | |
| 2013/0079621 A1* | 3/2013 | Shoham | A61M 37/0092 600/407 |
| 2015/0217142 A1* | 8/2015 | Schafer | A61N 7/00 601/2 |
| 2015/0283277 A1* | 10/2015 | Schafer | A61N 5/0624 422/20 |

OTHER PUBLICATIONS

Farny et al. 2005 Acoustics Research Letters Online 6:138-143 (Year: 2005).*
U.S. Appl. No. 62/330,699, filed May 2, 2016, Yang, et al.
Cui, H., et al., Laser-enhanced cavitation during high intensity focused ultrasound: An in vivo study. Appl Phys Lett. Apr. 1, 2013; 102(13): 133702; 4 pages.
Cui, H., et al., Laser enhanced high-intensity focused ultrasound thrombolysis: An in vitro study. J Acoust Soc Am. Feb. 2013; 133(2): EL123-EL128; 6 pages.

* cited by examiner

METHOD AND APPARATUS FOR REMOVING MICROVESSELS

CROSS-REFERENCE TO RELATED APPLICATIONS

The present application claims priority to and the benefit of U.S. Provisional Patent Application Ser. No. 62/330,699 titled "METHOD AND APPARATUS FOR REMOVING MICROVESSELS" filed May 2, 2016, the disclosure of which is incorporated herein by reference in its entirety.

STATEMENT OF GOVERNMENT INTEREST

This invention was made with government support under Grant Nos. EY022299 and CA186769 awarded by the National Institutes of Health. The government has certain rights in the invention.

BACKGROUND OF THE DISCLOSURE

Angiogenesis plays a critical role in the pathogenesis of numerous pathological conditions, including cancer, inflammation, and eye diseases. Significant research efforts have, therefore, been focused on the development of antivascular therapies, which include anti-angiogenic and vascular targeting therapies. Whereas anti-angiogenic therapy aims to inhibit the growth of new vessels, vascular targeting therapy is designed to selectively destroy existing vessels. For example, angiogenesis inhibitors targeting the vascular endothelial growth factor (VEGF) signaling pathway have been developed to treat tumors and eye diseases. While these treatments have proven to be efficacious, like other pharmaceutical approaches, the systemic administration of drugs can cause serious adverse effects including stroke and heart attack, and patients may become drug-resistant. Moreover, several studies on cancer have shown that while there is an initial antitumor effects, relapse and progressive tumor growth often follows the use of angiogenesis inhibitors. Local administration of these pharmaceuticals (e.g. intravitreal injection), also carries local risks, including local infection (endophthalmitis), hemorrhage, cataract, and retinal tear and detachment.

Additional antivascular approaches include photodynamic therapy (PDT), embolotherapy, antivascular ultrasound therapy (AVUT), and photothermolysis. These approaches have been developed to shut down or destroy existing blood vessels. Each of these methods has limitations affecting its utility, including being invasive in all three vascular-selective methods. PDT requires the systemic injection of photosensitizers, making the skin and eyes sensitive to light after the treatment. PDT may also cause burns, swelling, pain, and scarring in nearby healthy tissue and if it extravasates during intravenous injection. PDT in ophthalmic applications has also been associated with choroidal infarction and acute, severe vision loss.

Embolotherapy, on the other hand, is an invasive procedure involving inserting a catheter through the vascular system to the origin of the vessel to be occluded, and then injecting an agent. This is performed to control bleeding, close fistulae or arteriovenous malformations, devascularize organs, and reduce tumors or varicoceles.

AVUT has demonstrated the capability of removing microvessels in murine tumors with the assistance of microbubbles, via disruption or embolization. However, similar to PDT and embolotherapy, AVUT requires the systemic injection of foreign particles (bubbles) into the blood stream, which leads to serious concerns of toxicity, efficiency, and emboli formation. In addition, very strict treatment time window is also a major concern in clinical adaptions of both PDT and AVUT because the circulation time of photosensitizers and microbubbles is limited. This limits the clinical applicability, particularly in high volume retinal practices, where PDT causes a significant disruption in clinic flow.

Photothermolysis is a selective therapeutic technique based on optical absorption to remove and/or ablate tissue. It does not necessarily specifically target vasculature. By using milli- or micro-second laser pulses, photothermolysis can remove optically absorptive targets such as pigmented structures and cells. However, photothermolysis requires high laser energy. Because it relies on the thermal effect, clinical application of the photothermolysis laser is limited to very superficial surface layer.

SUMMARY

In some embodiments, a system for removing microvessels includes an acoustic energy source, an optical energy source, and a final lens. The acoustic energy source is configured to provide an acoustic energy at a target location. The optical energy source is configured to provide an optical energy at the target location such that the acoustic energy and the optical energy at least partially overlap at the target location. The final lens is positioned proximate the target location to defocus the optical energy toward the target location.

In other embodiments, a computer readable medium contains instruction that, when read by a computing device, cause the computing device to perform a method of removing microvessels. The method includes providing an acoustic energy to a target location and providing an optical energy to the target location concurrently with the acoustic energy. The acoustic energy has a pressure insufficient to cause cavitation in blood alone. The optical energy has a fluence insufficient to cause to cause cavitation in blood alone. The combination of the pressure of the acoustic energy and the fluence of the optical energy causes cavitation in blood.

In yet other embodiments, a method of removing microvessels includes applying a burst of acoustic energy at a target location, applying a pulse of optical energy at the target location, and promoting cavitation at the target location. The burst of acoustic energy has a pressure below 5.0 MPa. The pulse of optical energy at the target location has a fluence less than 100 mJ/cm$^2$. At least a portion of the pulse is concurrent with the burst and the optical energy has an optical area that is overlapping with an acoustic area of the acoustic energy at the target location.

This summary is provided to introduce a selection of concepts that are further described below in the detailed description. This summary is not intended to identify key or essential features of the claimed subject matter, nor is it intended to be used as an aid in limiting the scope of the claimed subject matter.

Additional features and advantages of embodiments of the disclosure will be set forth in the description which follows, and in part will be obvious from the description, or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

This disclosure generally relates to devices, systems, and methods for removing microvessels in an organism. More particularly, this disclosure relates to the combined use of optical energy and acoustic energy to selectively target and remove microvessels. In some embodiments, systems and methods of photo-mediated ultrasound therapy (PUT) described in the present disclosure may allow microvessel removal with increased precision and/or selectivity when compared to conventional therapies while remaining an agent-free treatment.

PUT includes a combined use of optical energy and acoustic energy to selectively target specific tissue or material in a body. The increased selectivity of PUT compared to conventional therapies may be at least partially related to the endogenous optical contrast between tissue types. Different tissues in an organism contain different concentrations of various chromophores and have different optical absorption spectra. The optical absorption spectra can facilitate the differentiation of tissue types with multi-spectral optical techniques that are highly sensitive and specific. PUT has the unique capability to target, without any exogenous agent, blood vessels by taking advantage of the high native contrast in the optical absorption between hemoglobin, melanin, and other tissues. Since hemoglobin absorbs more optical energy than other tissues at certain wavelengths, excitation (and cavitation) is limited to blood vessels, and hence, the treatment is highly localized. Additionally, oxygenated hemoglobin ($HbO_2$) and deoxygenated hemoglobin (HbR) have different optical absorption spectra, allowing selective treatment of either vein or artery by using PUT. In contrast to conventional therapeutic techniques utilizing ultrasound contrast agents and/or nanoparticles to catalyze cavitation, PUT may produce cavitation in the targeted blood vessel without additional agents and selectively at the confluence of the applied optical energy and acoustic energy.

The combination of the optical energy and acoustic energy may produce photospallation. Photospallation is the creation of thermoelastic stress in the vessel via the photoacoustic effect. Upon application of the optical energy, a photoacoustic wave is produced in the microvessel that converges in the center of the cylindrical microvessel. The convergence of the photoacoustic wave produces a low-pressure region in the microvessel. Further application of acoustic energy to the microvessel may superpose to the photoacoustic wave and result in cavitation. The oscillating cavitation in the microvessel may then apply mechanical stresses to the vasculature and impact the physiological functions of vascular endothelial cells (ECs), red blood cells, and platelets, resulting in vasocontraction and blood clot formation.

Figure 1:
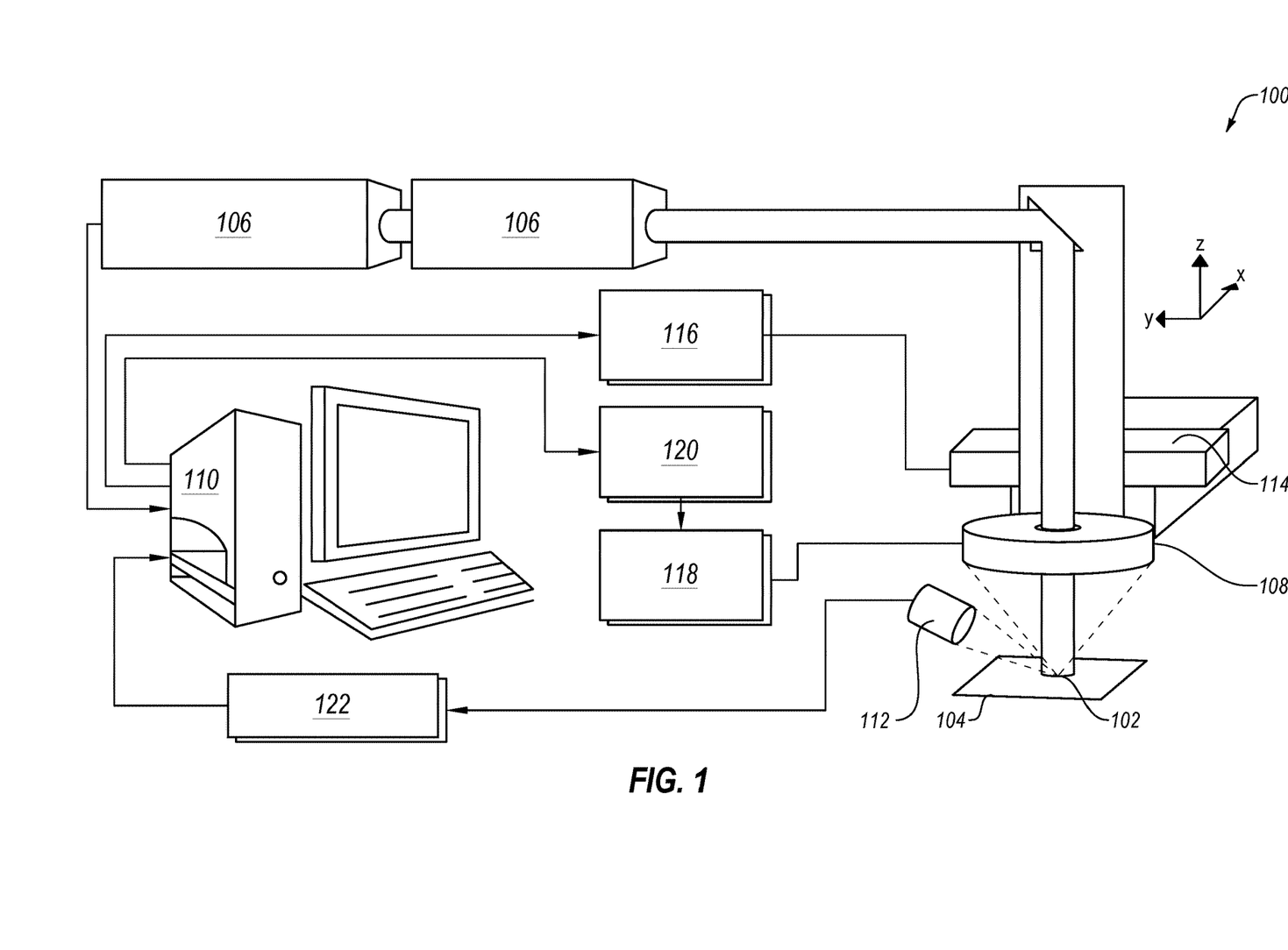
FIG. 1 is a schematic view of an embodiment of a system for removing microvessels, according to at least one embodiment of the present disclosure.

FIG. 1 is a schematic representation of an embodiment of a system 100 for removing microvessels. In some embodiments, a system 100 may be configured to provide PUT to a target location 102 on a tissue 104. In other embodiments, the system 100 may include one or more degrees of freedom to direct the optical energy and acoustic energy to a plurality of target locations 102 in a region of the tissue 104 to remove microvessels over a larger area than the target location 102 alone.

The tissue 104 targeted by the system 100 may be any tissue 104 with one or more microvessels. In some examples, the tissue 104 may be dermatological tissue, such as the dermis or abnormal growths in the dermis (i.e., lesions). In other examples, the tissue 104 may be muscular tissue. In other examples, the tissue 104 may part of one or more internal organs of the body. While the use of the system 100 may be described herein primarily in relation to ocular tissue (e.g., as described in relation to FIG. 2, FIG. 6, and FIGS. 8A and 8B), it should be understood that the presently described system may promote cavitation in any tissue containing microvessels.

The system 100 includes an optical energy source 106 and an acoustic energy source 108. The optical energy source 106 and acoustic energy source 108 may be confocal at the target location 102. In some embodiments, the optical energy source 106 and/or acoustic energy source 108 may be operated in a series of pulses. For example, the optical energy source 106 may be pulsed such that at least a portion of the pulse temporally overlaps with a pulse of the acoustic energy source 108. In other examples, the optical energy source 106 may be pulsed during a continuous operation of the acoustic energy source 108. In yet other examples, the optical energy source 106 may be operated continuously while the acoustic energy source 108 is pulsed during the operation of the optical energy source 106.

In some embodiments, the optical energy source 106 and/or the acoustic energy source 108 may be controlled at by a computing device 110. In at least one embodiment, the computing device 110 may include or be in communication with a computer readable medium (CRM) that may contain instructions that, when read by the computing device, cause the computing device to perform one or more methods described herein. For example, the timing of the optical energy source 106 pulse and the acoustic energy source 108 pulse may be coordinated by the computing device 110. In other examples, a series of overlapping pulses from the optical energy source 106 and acoustic energy source 108 may be controlled by the computing device 110. In yet other examples, the computing device 110 may be in communication with one or more sensors 112 configured to detect cavitation or other aspects of the target location 102 and/or tissue 104. In such examples, the computing device 110 may pulse the optical energy source 106 and/or acoustic energy source 108 based at least partially on information communicated by the one or more sensors 112.

In some embodiments, the system 100 may include further components to increase the performance and/or versatility of the system 100. For example, the system 100 may include a stage 114 that supports one or more components of the optical energy source 106 and/or the acoustic energy source 108. Movement of the stage 114 may allow for the system to direct the optical energy and acoustic energy at a plurality of target locations 102. In some embodiments, the stage 114 may be a motorized stage in communication with and/or configured to receive instructions from a motor controller 116. In other embodiments, the stage 114 may be in communication with and/or may receive instructions from the computing device 110. In some embodiments, the stage 114 may provide a first degree of freedom, allowing the system 100 to deliver energy to a plurality of target locations in a line. In other embodiments, the stage 114 may have a plurality of degrees of movement to allow the system 100 to deliver energy to a plurality of target locations in an area. In at least one embodiment, the stage 114 may include a tilt degree of freedom, allowing the system 100 to alter the angle at which the energy is delivered to the target location.

In some embodiments, the system 100 may include one or more components to provide additional control over the delivery of acoustic energy. For example, the system 100 may include one or more power amplifiers 118 in communication with the acoustic energy source 108. In examples, the system 100 may include one or more function generators 120 in communication with the acoustic energy source 108 to control the phase and/or frequency of the acoustic energy from the acoustic energy source 108.

In some embodiments, the system 100 may include one or more components to provide additional control over the one or more sensors 112. For example, the system 100 may include one or more pre-amplifiers 122 in communication with the one or more sensors 112, to increase the received signal from the one or more sensors 112 that is provided to the computing device 110.

Figure 2:
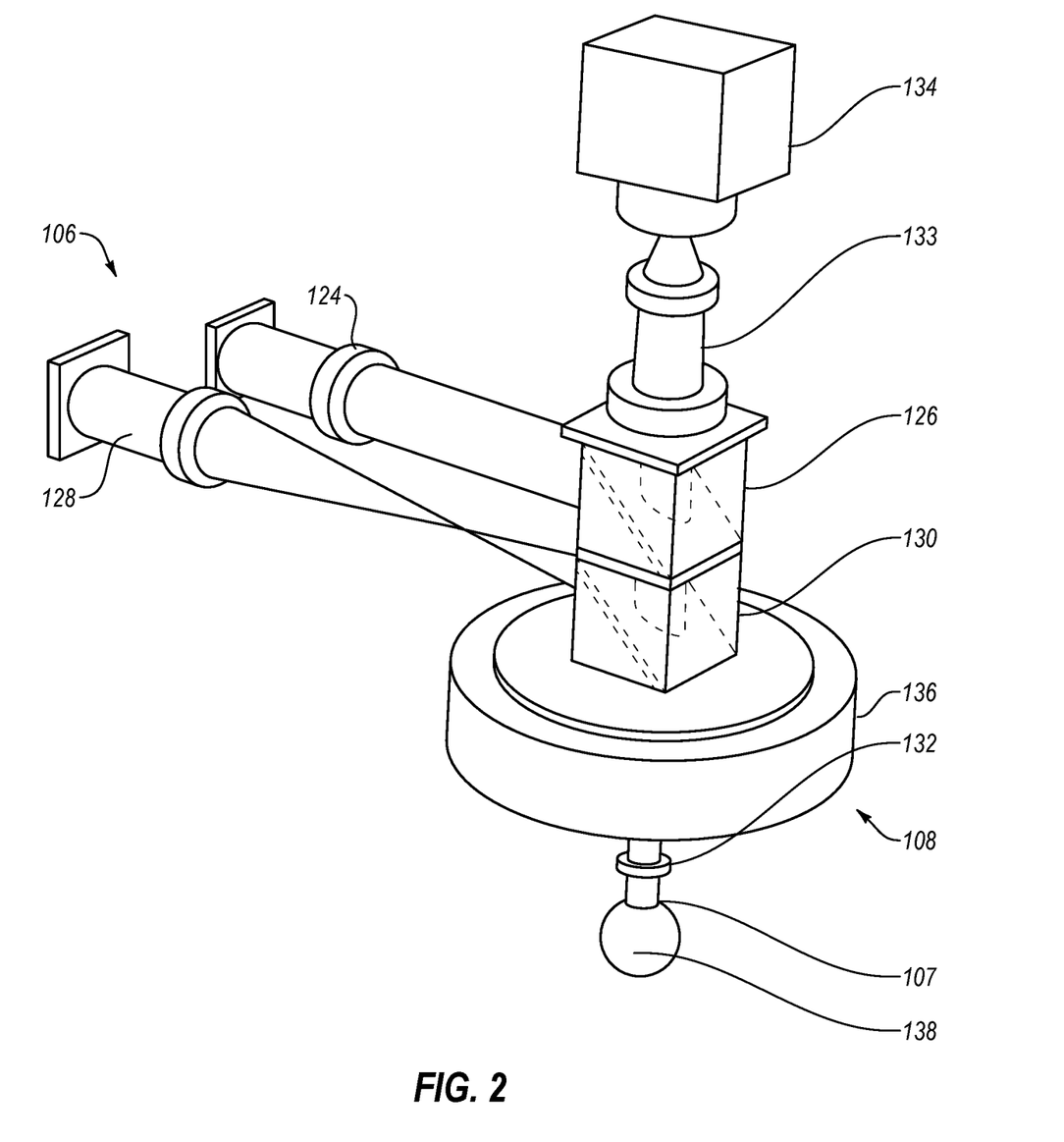
FIG. 2 is a perspective view of an embodiment of a system for removing microvessels in an eye, according to at least one embodiment of the present disclosure.

FIG. 2 is a perspective view of an embodiment of the optical energy source 106 optics stack and the acoustic energy source 108. In some embodiments, the optical energy source 106 may include one or more lasers. For example, the optical energy source may include an yttrium aluminum garnet (YAG) laser. A neodymium-doped yttrium aluminum garnet (Nd:YAG) pumped optical parametric oscillator (OPO) system may be used as the optical energy source 106 for PUT. The optical energy source 106 may have a peak wavelength in the tuning range. In some embodiments, the peak wavelength may be in a range having an upper value, a lower value, or an upper and lower value including any of 400 nm, 600 nm, 800 nm, 1000 nm, 1200 nm, 1400 nm, 1600 nm, 1800 nm, 2000 nm, 2200 nm, 2400 nm, or any values therebetween. For example, the peak wavelength may be greater than 400 nm. In other examples, the peak wavelength may be less than 2400 nm. In yet other examples the peak wavelength may be in a range of 400 nm to 2400 nm. In further other examples, the peak wavelength may be in a range of 450 nm to 1600 nm. In at least one example, the peak wavelength may be tuned to the peak optical absorption wavelength of the target material, such as hemoglobin.

The optical energy source 106 may operate at a repetition rate with a pulse duration. In some embodiments, the optical energy source 106 may be operated at a repetition rate in a range having an upper value, a lower value, or upper and lower values including any of 2 Hz, 4 Hz, 6 Hz, 8 Hz, 10 Hz, 15 Hz, 20 Hz, 40 Hz, or any values therebetween. For example, the repetition rate may be greater than 2 Hz. In other examples, the repetition rate may be less than 40 Hz. In yet other examples, the repetition rate may be in a range of 2 Hz to 40 Hz. In further examples, the repetition rate may be between 6 Hz and 20 Hz. In at least one example, the repetition rate may be 10 Hz.

In some embodiments, the pulse duration may be in a range having an upper value, a lower value, or upper and lower values including any of 0.1 nanosecond (ns), 0.5 ns, 1 ns, 2 ns, 3 ns, 4 ns, 5 ns, 6 ns, 7 ns, 8 ns, 9 ns, 10 ns, or any values therebetween. For example, the pulse duration may be greater than 0.1 ns. In other examples, the pulse duration may be less than 10 ns. In yet other examples, the pulse duration may be between 0.1 ns and 10 ns. In further examples, the pulse duration may be between 2 ns and 6 ns. In at least one example, the pulse duration may be 4 ns.

The optical energy source may include one or more lenses 124 or other optical components to direct the optical energy into a first prism 126. The first prism 126 may combine optical signals from the optical energy source 106 and a visual monitoring system including an illumination source 128 and a camera 134. In some embodiments, the illumination source 128 may be ring illumination source that provides an annular illumination to the target location 102. The visual monitoring system may allow a user or a computer to visually monitor the progress of the microvessel removal. The illumination source 128 may provide illumination through a second prism 130 that combines the illumination with the optical energy from the optical energy source 106.

In some embodiments, a final lens 132 may be positioned in line with the optical energy and illumination to direct the optical energy and illumination at a target location 102. For example, when directing optical energy at a location in an eye 138, the optical energy may pass through a lens of the eye 138. To ensure the optical energy is focused at the target location 102, the final lens 132 may defocus the optical energy prior to passing through the lens of the eye 138. The optical energy is delivered to the target location 102 and the surface fluence is monitored and controlled during application using one or more sensors and/or the camera 134.

In some embodiments, the fluence may be in a range having an upper value, a lower value, or upper and lower values including any of 1 mJ/cm$^2$, 2 mJ/cm$^2$, 4 mJ/cm$^2$, 6 mJ/cm$^2$, 8 mJ/cm$^2$, 10 mJ/cm$^2$, 15 mJ/cm$^2$, 20 mJ/cm$^2$, 25 mJ/cm$^2$, 30 mJ/cm$^2$, 35 mJ/cm$^2$, 40 mJ/cm$^2$, 60 mJ/cm$^2$, 80 mJ/cm$^2$, 100 mJ/cm$^2$, or any values therebetween. For example, the fluence may be greater than 1 mJ/cm$^2$. In other examples, the fluence may be less than 100 mJ/cm$^2$. In yet other examples, the fluence may be between 1 mJ/cm$^2$ and 100 mJ/cm$^2$. In further examples, the fluence may be between 2 mJ/cm$^2$ and 80 mJ/cm$^2$. In yet further examples, the fluence may be between 3 mJ/cm$^2$ and 60 mJ/cm$^2$. In at least one example, the fluence may be 4 mJ/cm$^2$.

Acoustic energy may be applied to the target location 102 in addition to the optical energy. In some embodiments, a therapeutic ultrasound transducer 136 may be positioned near or adjacent the target location 102. The therapeutic ultrasound transducer 136 may be used to supply ultrasound bursts to the target location 102. A hole in the middle of the therapeutic ultrasound transducer 136 may allow the optical energy to pass through the therapeutic ultrasound transducer 136. The therapeutic ultrasound transducer 136 may produce an ultrasound pulse through the center of the therapeutic ultrasound transducer 136 that is overlapping the optical energy passing through the therapeutic ultrasound transducer 136.

In some embodiments, a therapeutic ultrasound transducer 136 may use an electric potential and/or current to move one or more components of the therapeutic ultrasound transducer 136 and produce an acoustic wave. The annular structure of the therapeutic ultrasound transducer 136 may assist in focusing the acoustic wave through the center of the therapeutic ultrasound transducer 136 and directing the acoustic energy to the target location 102. Application of the optical energy or the acoustic energy individually is insufficient to promote cavitation in microvessels. The concurrent application of the optical energy and the acoustic energy may promote cavitation that inhibits the activity and/or growth of the microvessels.

Figure 3:
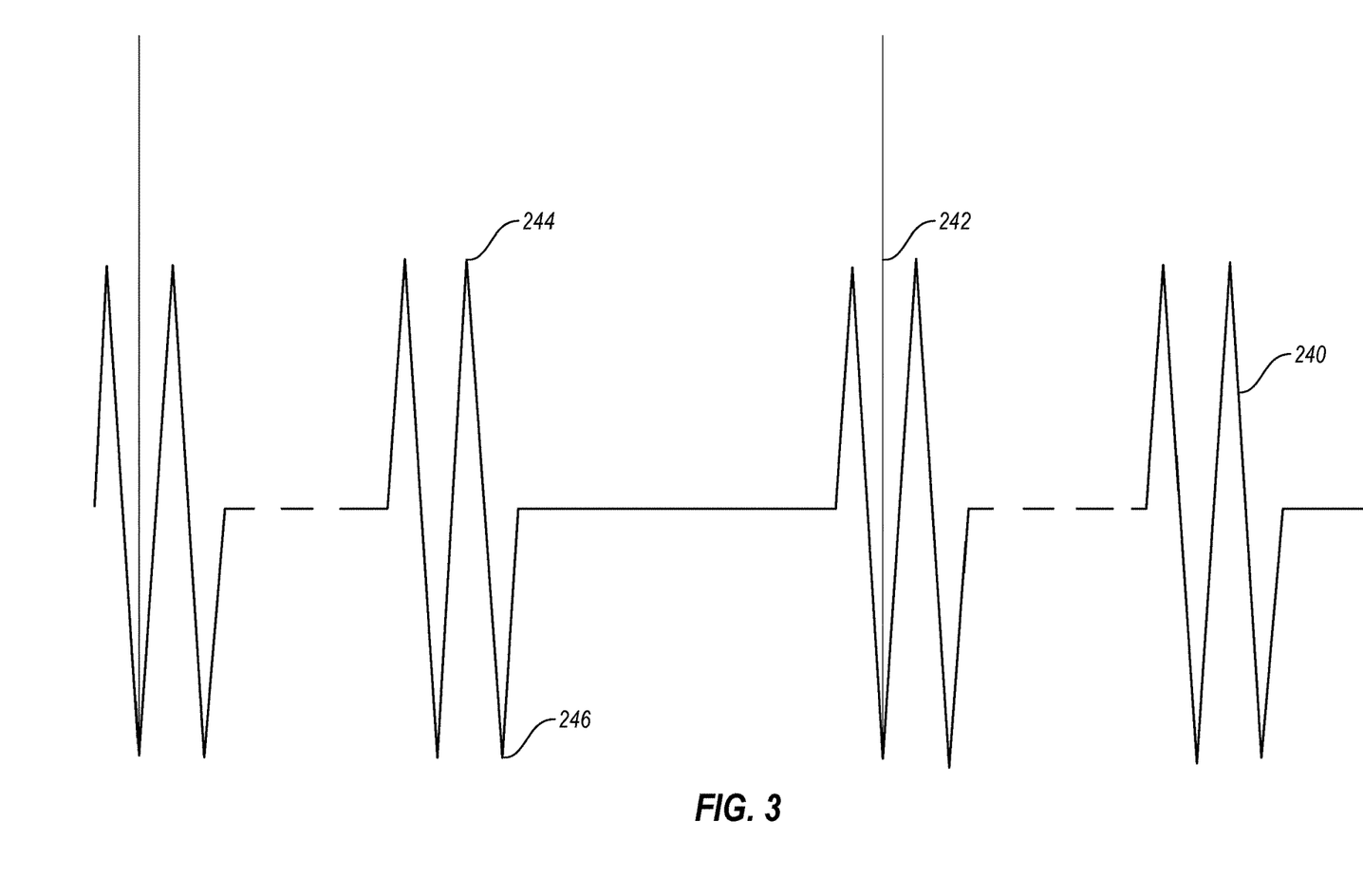
FIG. 3 is a graph illustrating an embodiment of a timing of bursts of acoustic energy and pulses of optical energy, according to at least one embodiment of the present disclosure.

FIG. 3 schematically illustrates the timing of the acoustic energy 240 of a therapeutic ultrasound transducer and optical energy 242 from an optical energy source. Each burst of acoustic energy 240 has a series of positive pressures and negative pressures, each with a respective maximum positive pressure 244 and maximum negative pressure 246. The acoustic energy 240 may include one of more bursts in a sequence. In some embodiments, the sequence may have pauses (indicated by the dashed portion of the acoustic energy 240. The illustrated embodiment of acoustic energy 240 includes a sequence including two bursts followed by another sequence including two bursts.

In some embodiments, a laser pulse is delivered to the target location to overlay the rarefaction phase (maximum negative pressure 246) at the beginning of each ultrasound burst. Timing of the concurrent energy delivery during rarefaction increases the likelihood of cavitation according to the underlying mechanism. In other embodiments, a laser pulse is delivered to the target location to overlay each rarefaction phase (maximum negative pressure 246) during each ultrasound burst.

In some embodiments, the therapeutic ultrasound transducer may provide acoustic energy with a maximum positive pressure 244 and/or maximum negative pressure 246 (below atmosphere) in a range having an upper value, a lower value, or upper and lower values including any of 0.1 Megapascals (MPa), 0.2 MPa, 0.3 MPa, 0.4 MPa, 0.5 MPa, 0.6 MPa, 0.8 MPa, 1.0 MPa, 1.2 MPa, 1.4 MPa, 1.6 MPa, 1.8 MPa, 2.0 MPa, 2.5 MPa, 3.0 MPa, 4.0 MPa, 5.0 MPa, or any values therebetween. For example, the pressure maximum may be greater than 0.1 MPa. In other examples, the pressure maximum may be less than 5.0 MPa. In yet other examples, the pressure maximum may be between 0.1 MPa and 5.0 MPa. In further examples, the pressure maximum may be between 0.2 MPa and 2.5 MPa. In yet further examples, the pressure maximum may be between 0.3 MPa and 2.0 MPa. In at least one example, the pressure maximum may be 0.45 MPa.

In some embodiments, the therapeutic ultrasound transducer may provide acoustic energy with a frequency in a range having an upper value, a lower value, or upper and lower values including any of 500 kHz, 550 kHz, 600 kHz, 650 kHz, 700 kHz, 750 kHz, 800 kHz, 850 kHz, 900 kHz, 950 kHz, 1.0 MHz, or any values therebetween. For example, the frequency may be greater than 500 kHz. In other examples, the frequency may be less than 1.0 MHz. In yet other examples, the frequency may be between 500 kHz and 1.0 MHz. In further examples, the frequency may be between 550 kHz and 950 kHz. In yet further examples, the frequency may be between 600 kHz and 900 kHz. In at least one example, the frequency may be 750 kHz.

In some embodiments, the duty cycle of the therapeutic ultrasound transducer may be in a range having an upper value, a lower value, or upper and lower values including any of 0.1%, 1%, 2%, 3%, 4%, 5%, 6%, 7%, 8%, 9%, 10%, or any values therebetween. For example, the duty cycle may be greater than 0.1%. In other examples, the duty cycle may be less than 10%. In yet other examples, the duty cycle may be between 0.1% and 10%. In further examples, the duty cycle may be between 2% and 9%. In yet further examples, the duty cycle of the therapeutic ultrasound transducer may be between 3% and 8% during operation.

In some embodiments, the treatment duration to remove microvessels in the target area may be in a range having an upper value, a lower value, or upper and lower values of 1 minute, 5 minutes, 10 minutes, 15 minutes, 30 minutes, 45 minutes, 60 minutes, 75 minutes, 90 minutes, 105 minutes, 120 minutes, or any values therebetween. For example, the treatment duration may be greater than 1 minutes. In other examples, the treatment duration may be less than 120 minutes (2 hours). In yet other examples, the treatment duration may be less than 90 minutes. In further examples, the treatment duration may be less than 60 minutes. In at least one example, the treatment duration may be between 15 minutes and 90 minutes.

The effect of cavitation produced in a blood vessel induced by PUT is modeled as described herein. The generation and propagation of photoacoustic waves in a blood vessel have been simulated. Because the blood viscosity is small, the photoacoustic wave generation and propagation in an inviscid medium can be modelled by:

$$\left(\nabla^2 - \frac{1}{c}\frac{\partial^2}{\partial t^2}\right)p(\vec{r},t) = -\frac{\beta}{C}\frac{\partial H(\vec{r},t)}{\partial t}$$

where $p(\vec{r}, t)$ is the acoustic pressure at location $\vec{r}$ and time t, c is the sound speed, β is the thermal coefficient of volume expansion, and $H(\vec{r}, t)$ is the heating function defined as the thermal energy converted per unit volume and per unit time. The Keller-Miksis equation may be used to describe the subsequent bubble dynamics:

$$\left(1 - \frac{\dot{R}}{c}\right) R\ddot{R} + \frac{3}{2}\left(1 - \frac{\dot{R}}{3c}\right)\dot{R}^2 = \frac{R}{\rho c}\frac{d}{dt}[p_B] + \frac{1}{\rho}\left(1 + \frac{\dot{R}}{c}\right)\left(p_B - p_\infty - p\left(t + \frac{R}{c}\right)\right)$$

where dots denote time derivatives, R is the bubble radius, t is time, c is the sound speed in the surrounding medium, ρ is the density of the surrounding medium, $p_\infty$ is the pressure at the infinity, p is the applied acoustic pressure, and $p_B$ is the pressure at the surrounding medium side of the interface between the medium and the bubble. $p_B$ is given by the following formula:

$$p_B = p_g - \frac{2\sigma}{R} - \frac{4\mu}{R}\dot{R}$$

where $p_g$ is the pressure inside the bubble, σ is the surface tension coefficient, and μ is the viscosity of the fluid.

The Keller-Miksis equation may calculate cavitation dynamics during PUT and the change in bubble radius when a cavitation nucleus with a size of 50 nm is present in the photoacoustic field. For example, the optical energy applied may generate a photoacoustic wave field that is sufficient to promote inertial cavitation (IC) at a known rate per the simulations described herein. When the synchronized photoacoustic pulse (from the optical energy) and the ultrasound pulse are applied, the oscillation of the bubble exhibits non-linearity.

Inertial cavitation is when a volume of liquid is subjected to a sufficiently low pressure. The liquid may rupture and form a bubble or cavity. In the presence of an acoustic field, the bubble may oscillate in radius and volume at a high rate. The oscillation of the bubbles in the IC may be measured independently of non-inertial cavitation (when the intensity of the acoustic field is insufficient to cause total bubble collapse) occurring in the vessel by use of separate cavitation detectors.

Figure 4:
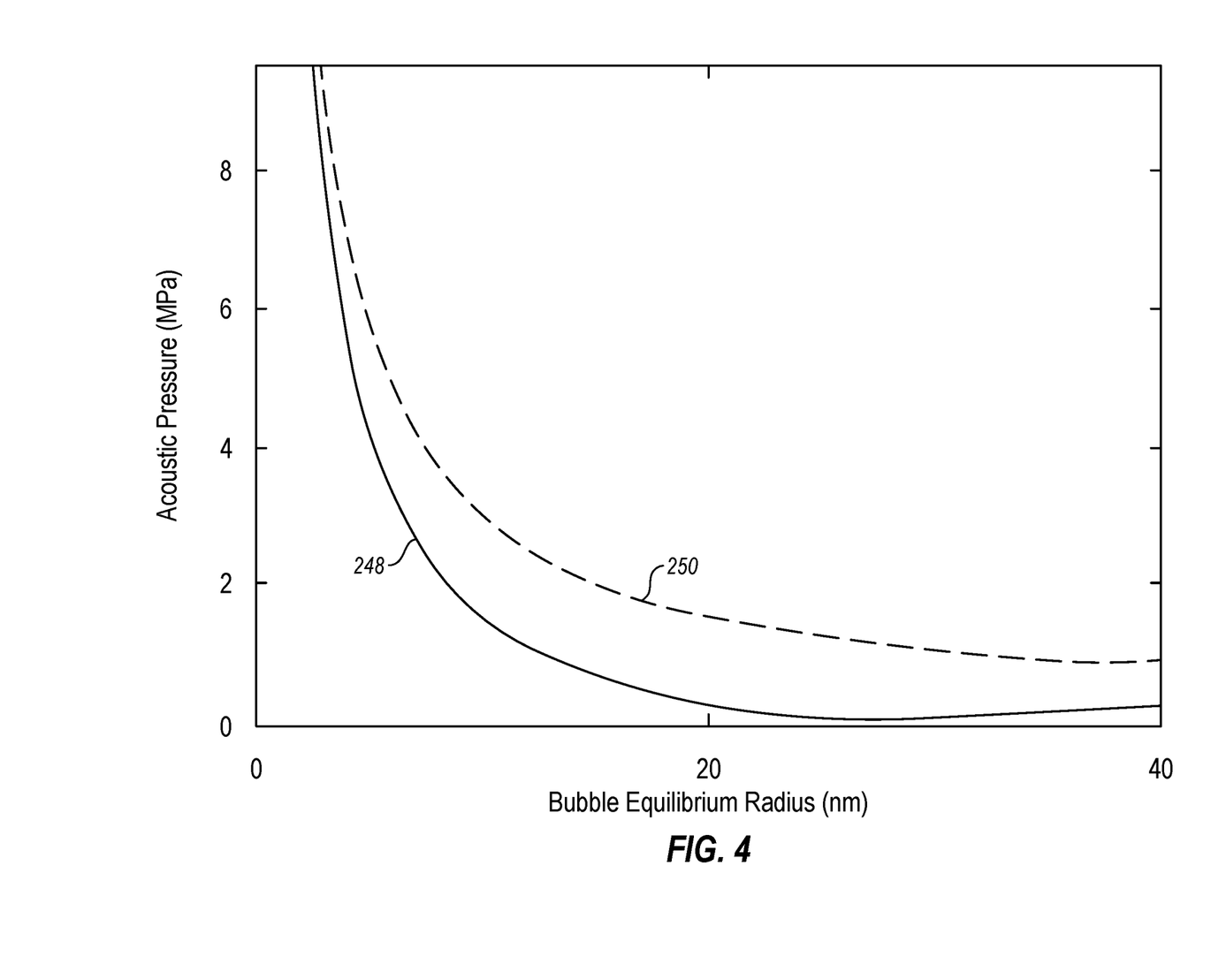
FIG. 4 is a graph illustrating an embodiment of cavitation bubble radii with and without a photoacoustic wave, according to at least one embodiment of the present disclosure.

FIG. 4 shows an embodiment of the calculated IC threshold with concurrently applied optical energy (i.e., photoacoustic wave) 248, and without concurrently applied optical energy 250. The superposition of the photoacoustic wave may reduce the pressure threshold for cavitation, indicating that the likelihood of cavitation will greatly increase as optical energy and acoustic energy are concurrently applied to a blood vessel.

Figure 5A:
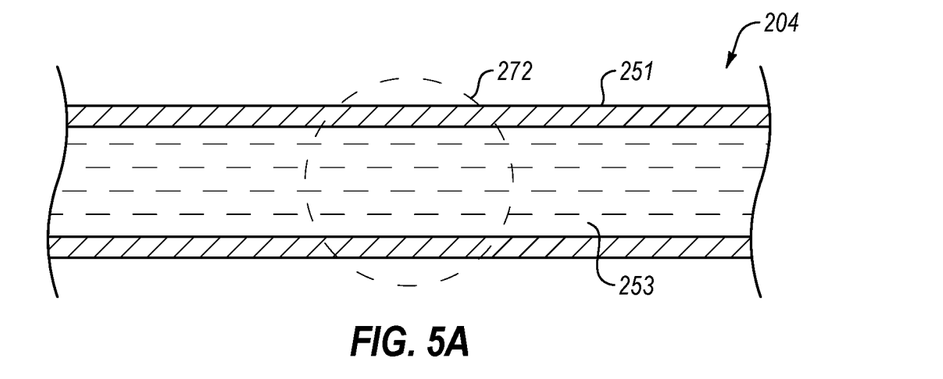
FIG. 5A is a side cross-sectional view of an embodiment of a microvessel exposed to acoustic energy at a target location, according to at least one embodiment of the present disclosure.
Figure 5B:
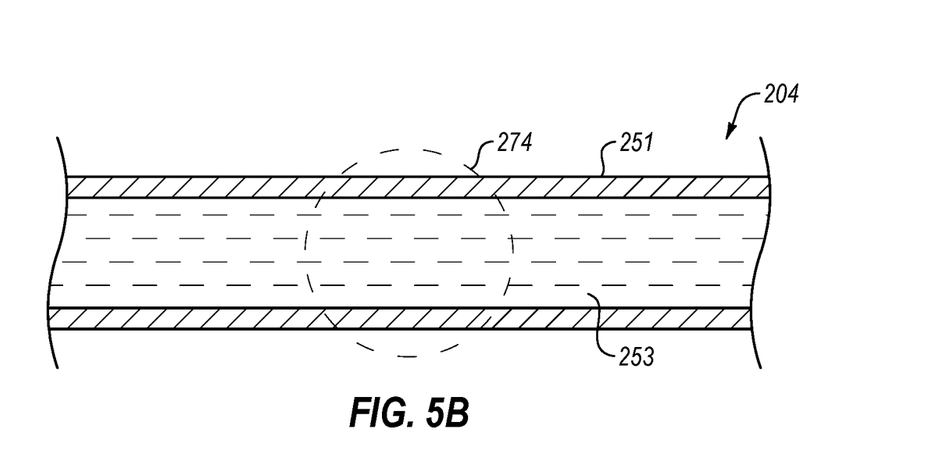
FIG. 5B is a side cross-sectional view of an embodiment of a microvessel exposed to optical energy at a target location, according to at least one embodiment of the present disclosure.
Figure 5C:
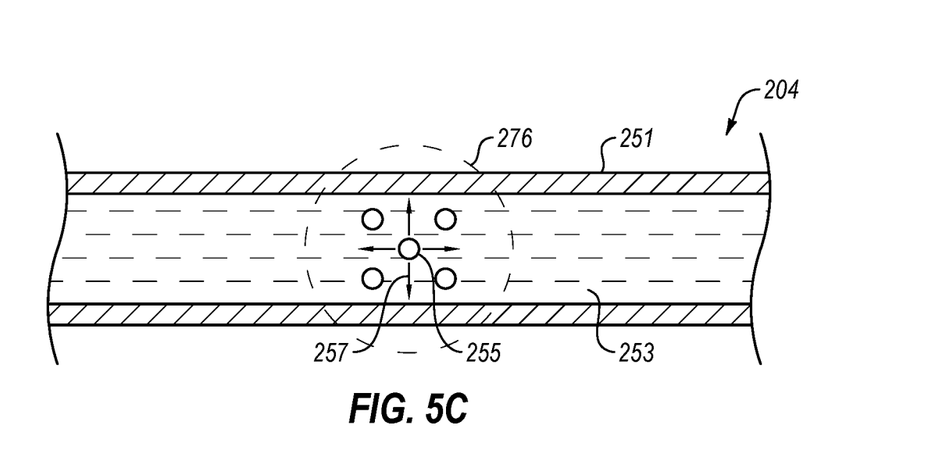
FIG. 5C is a side cross-sectional view of the microvessel of FIG. 5A exposed to optical energy concurrently with acoustic energy, according to at least one embodiment of the present disclosure.

FIGS. 5A, 5B, and 5C illustrate the results of an experiment under the described conditions. The photoacoustic signal detected during the experiment indicates the amount of cavitation occurring in the target location and/or microvessel. FIG. 5A is a side cross-sectional view of an embodiment of a microvessel 251 in a tissue 204 with acoustic energy applied alone. The microvessel 251 contains a fluid 253, such a hemoglobin or other bodily fluid. In some examples, the microvessel 251 may be an artery where the fluid 253 is oxygenated hemoglobin. In other examples, the microvessel 251 may be a vein where the fluid 253 is deoxygenate hemoglobin. In yet other examples, the microvessel 251 may be another vessel of the body containing another fluid 253. In the experiment, an acoustic energy at 0.45 MPa at 1.0 MHz with 4% duty cycle was applied in an acoustic area 272 to the microvessel 251 and fluid 253. The changes in photoacoustic signal before and after application of the acoustic energy from a therapeutic ultrasound transducer alone were within the measurement error.

FIG. 5B is a side cross-sectional view of the embodiment of a microvessel 251 in tissue 204 of FIG. 5A with optical energy applied alone. In the experiment, an optical energy of 20 mJ/cm² and a wavelength of 570 nm was applied in an optical area 274 to the microvessel 251 and fluid 253. The changes in photoacoustic signal before and after application of the optical energy from a laser only were within the measurement error.

FIG. 5C is a side cross-sectional view of the embodiment of a microvessel 251 in tissue 204 of FIG. 5A with optical energy and acoustic energy applied concurrently in an active area 276. The acoustic energy was 0.45 MPa at 1.0 MHz with a 4% duty cycle and the optical energy was 20 mJ/cm² and a wavelength of 570 nm. The concurrent application of the acoustic energy and optical energy produced observable cavitation in the fluid 253. Bubbles 255 forming in the fluid 253 oscillated in diameter, applying a pressure 257 radially outward from the bubbles 255 to the microvessel 251. Cavitation was observed only when ultrasound and laser were applied concurrently.

Figure 6:
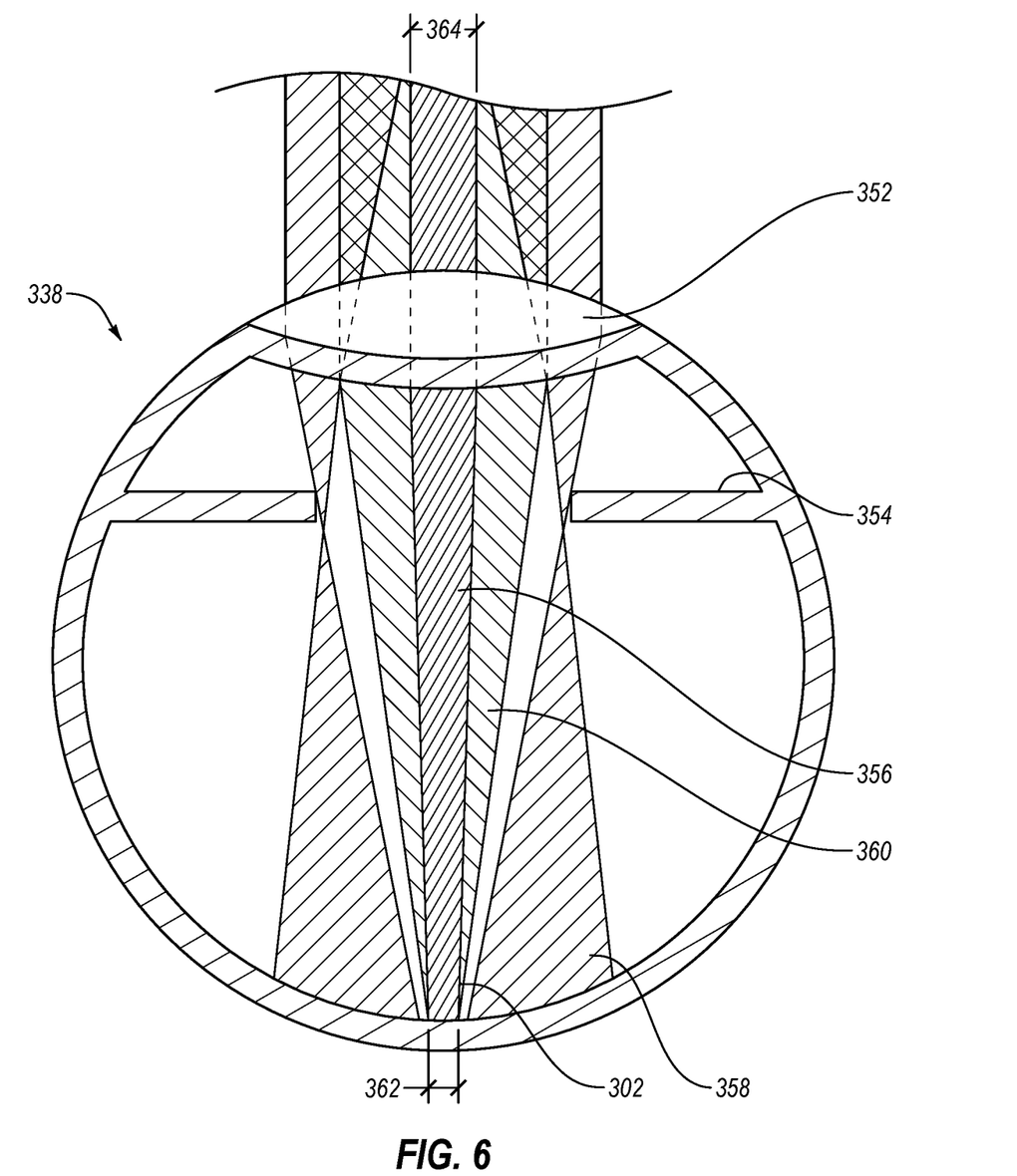
FIG. 6 is a side cross-sectional view of an embodiment of application of optical energy at a target location in an eye, according to at least one embodiment of the present disclosure.

FIG. 6 illustrates an embodiment of optical energies interacting with an eye 338 to apply optical energy to a target location 302. The optical energy may interact with a lens 352 and an iris 354 of the eye 338 on route to the target location 302. In some embodiments, a therapeutic optical energy 356 and an illumination light 358 are applied concurrently. The therapeutic optical energy 356 may be provided by a laser as described herein. The illumination light 358 may provide imaging of the blood vessels by illuminating the choroid using a polarized annular-structure pattern. In some embodiments, the illumination light 358 may be focused onto the pupil plane to minimize back-reflections from the clear ocular media. The annular illumination light 358 is relayed from an annular-shaped source and combined with the therapeutic optical energy 356 path using a polarizing beamsplitter.

In some embodiments, the final spot size 362 of the therapeutic optical energy 356 may be less than an initial spot size 364. For example, the lens 352 of the eye 338 may further focus the therapeutic optical energy 356 down to a smaller size. In some embodiments, the final spot size 362 at a target location 302 may be in a range having a lower value, an upper value, or upper and lower values including any of 0.01 millimeters (mm), 0.1 mm, 0.2 mm, 0.3 mm, 0.4 mm, 0.6 mm, 0.8 mm, 1.0 mm, 1.2 mm, 1.4 mm, 1.6 mm, 1.8 mm, 2.0 mm, 2.5 mm, 3.0 mm, or any values therebetween. For example, the final spot size 362 at the target location may be greater than 0.01 mm. In other examples, the final spot size 362 may be less than 3.0 mm. In yet other examples, the final spot size 362 may be between 0.01 mm and 3.0 mm. In further examples, the final spot size 362 may be between 0.5 mm and 2.0 mm. In at least one example, the final spot size 362 may be about 1.0 mm.

In some embodiments, the initial spot size 364 after the final lens (such as final lens 132 of FIG. 2) may be in a range having an upper value, a lower value, or upper and lower values including any of 1.0 mm, 1.2 mm, 1.4 mm, 1.6 mm, 1.8 mm, 2.0 mm, 2.2 mm, 2.4 mm, 2.6 mm, 2.8 mm, 3.0 mm, 3.2 mm, 3.4 mm, 3.6 mm, 3.8 mm, 4.0 mm, 4.2 mm, 4.4 mm, 4.6 mm, 4.8 mm, 5.0 mm, or any values therebetween. For example, the initial spot size 364 may be greater than 1.0 mm. In other examples, the initial spot size 364 may be less than 5.0 mm. In yet other examples, the initial spot size 362 may be between 1.0 mm and 5.0 mm. In further examples, the initial spot size 364 may be between 1.5 mm and 4.5 mm. In yet further examples, the initial spot size 364 may be between 2.0 mm and 4.0 mm. In at least one example, the initial spot size 364 may be 3.0 mm.

In some embodiments when removing microvessels in an eye 338, the initial spot size 364 and the final spot size 362 may have a spot size ratio (i.e., initial spot size 364 to final spot size 362) in a range having an upper value, a lower value, or upper and lower values including any of 1.1:1, 1.2:1, 1.3:1, 1.4:1, 1.5:1, 1.75:1, 2.0:1, 2.25:1, 2.5:1, 2.75:1, 3.0:1, or any values therebetween. For example, the spot size ratio may be greater than 1.1:1. In other examples, the spot size ratio may be less than 3.0:1. In yet other examples, the spot size ratio may be between 1.1:1 and 3.0:1. In further examples, the spot size ratio may be between 1.25:1 and 2.5:1. In yet further examples, the spot size ratio may be between 1.5:1 and 2.0:1.

Figure 7:
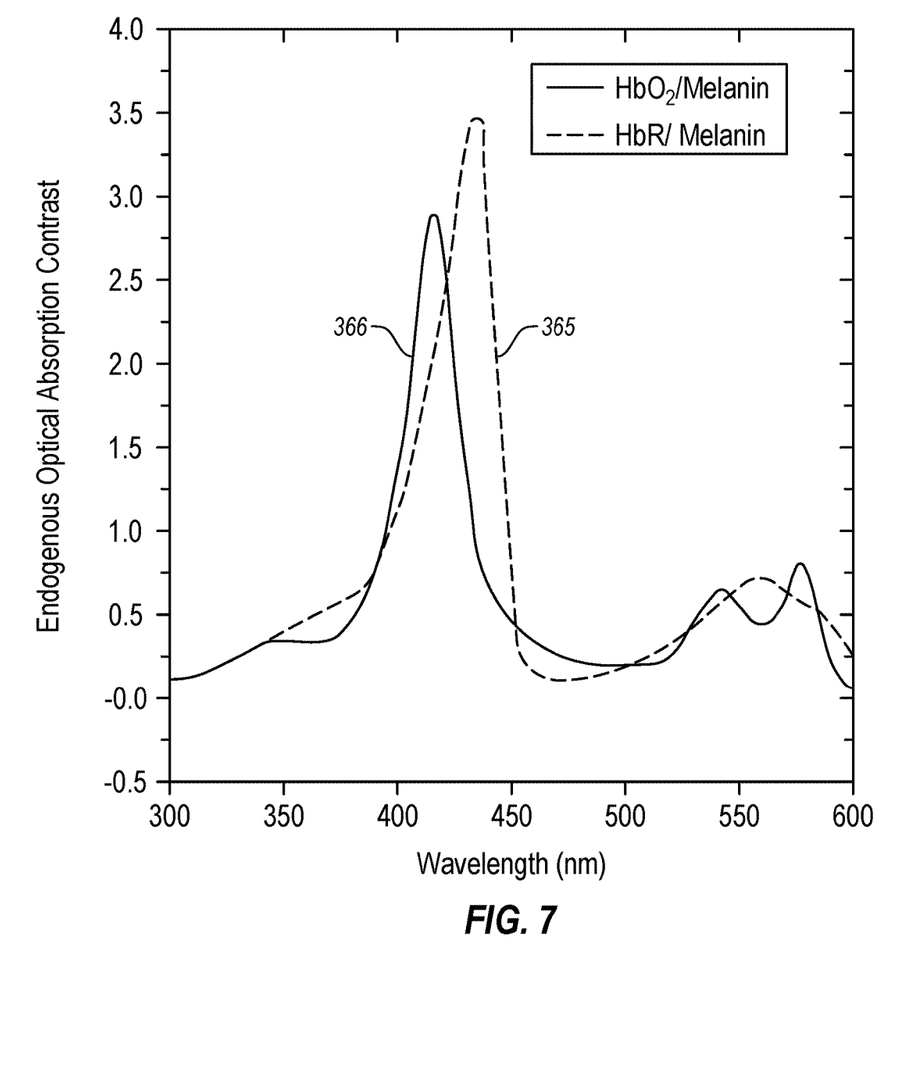
FIG. 7 is a graph illustrating the relative absorption contrast spectra of oxygenated and deoxygenated hemoglobin, according to at least one embodiment of the present disclosure.

As described herein, PUT can target blood vessels by taking advantage of the contrast in the optical absorption between hemoglobin, melanin, and other tissues. The contrast between oxygenated and deoxygenated hemoglobin further allows selective targeting of arteries versus veins. FIG. 7 is a chart illustrating the absorption spectrum of deoxygenated hemoglobin 365 (in veins) compared to melanin and the absorption spectrum of oxygenated hemoglobin 366 (in arteries) compared to melanin. The deoxygenated hemoglobin 365 has a contrast peak (3.5:1) compared to melanin at approximately 436 nm. The oxygenated hemoglobin 366 has a contrast peak (2.9:1) compared to melanin at approximately 418 nm. By tuning the optical energy source to the relative contrast peak, the optical energy source may selectively energize the hemoglobin in either an artery or a vein. In another example, the optical energy source may be tuned to another wavelength, such as a wavelength in between 500 nm and 600 nm to provide excitation to multiple absorption peaks of hemoglobin.

Figure 8A:
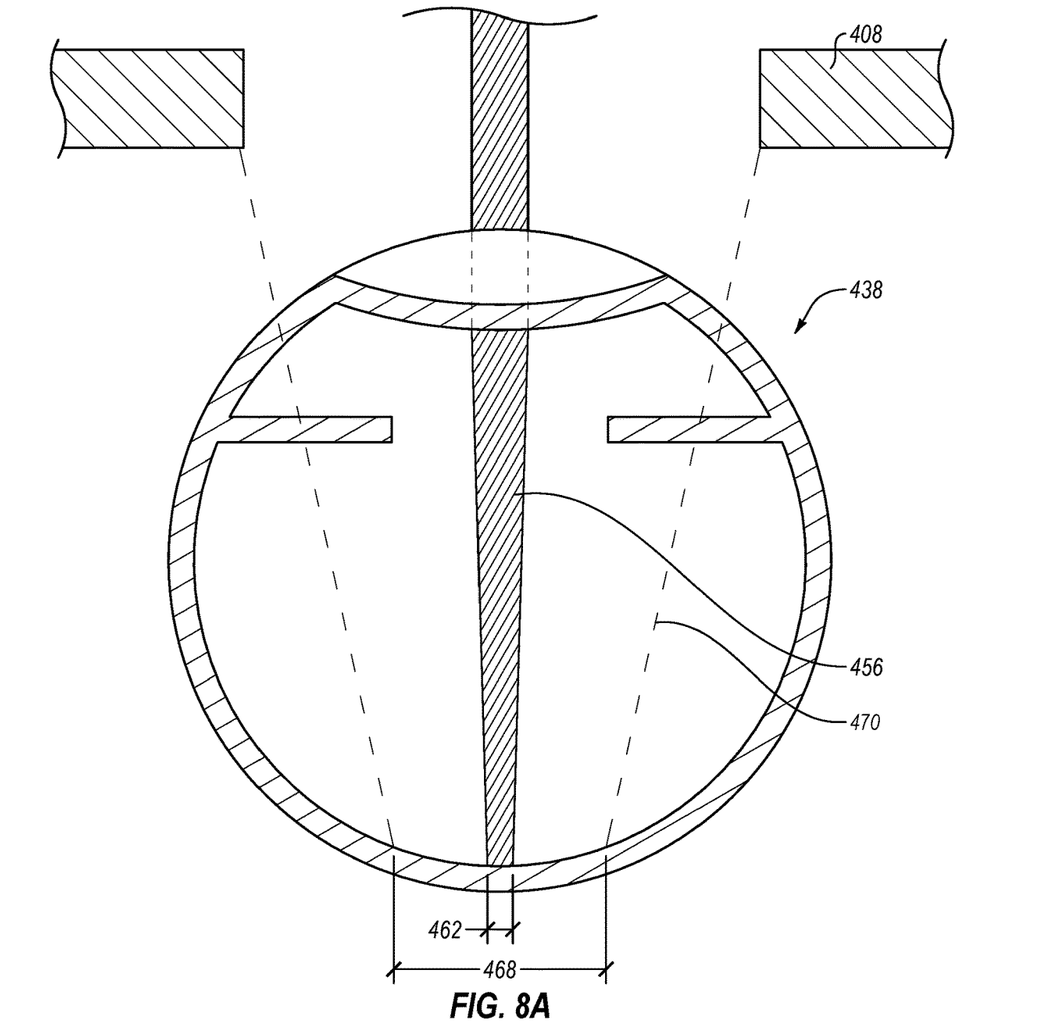
FIG. 8A is a side cross-sectional view of an embodiment of application of optical energy and acoustic energy at a target location in an eye, according to at least one embodiment of the present disclosure.

FIG. 8A is a schematic cross-sectional view of an embodiment of acoustic energy 470 and optical energy 456 applied in an eye 438. In some embodiments, the acoustic energy source 408 may focus acoustic energy 470 to an acoustic spot size 468 at the back of the eye 438 or other target location. The therapeutic optical energy 456 may be focused to a final spot size 462 within the acoustic spot size 468.

Figure 8B:
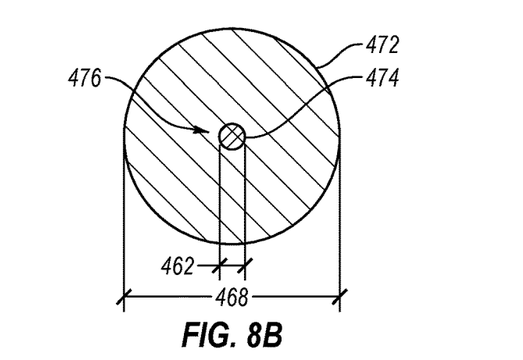
FIG. 8B is a top view of the relative position of the optical energy and acoustic energy of FIG. 8A, according to at least one embodiment of the present disclosure.

FIG. 8B is a top view of focal area of the acoustic energy and the optical energy of FIG. 8A. In some embodiments, the acoustic spot size 468 may correspond to an acoustic area 472 and the final spot size 462 of the optical energy may correspond to an optical area 474. In some embodiments, the acoustic area 472 may be substantially circular. In other embodiments, the acoustic area 472 may be elliptical and/or oblong with a major axis and a minor axis. In yet other embodiments, the acoustic area 472 may have one or more corners, such as a regular polygonal shape (e.g., square, equilateral triangle, hexagon, octagonal, etc.) or irregular polygonal shape (e.g., a rectangle, acute triangle, diamond, etc.). In further embodiments, the acoustic area 472 may be a combination of the foregoing.

In some embodiments, the optical area 474 may be substantially circular. In other embodiments, the optical area 474 may be elliptical and/or oblong with a major axis and a minor axis. In yet other embodiments, the optical area 474 may have one or more corners, such as a regular polygonal shape (e.g., square, equilateral triangle, hexagon, octagonal, etc.) or irregular polygonal shape (e.g., a rectangle, acute triangle, diamond, etc.). In further embodiments, the optical area 474 may be a combination of the foregoing.

In some embodiments, the acoustic area 472 and the optical area 474 may be concentric with one another. In other embodiments, the acoustic area 472 and the optical area 474 may completely overlap but not be concentric. In yet other embodiments, at least a portion of the optical area 474 may be positioned outside of the acoustic area 472.

In some embodiments, the acoustic spot size 468 of the acoustic area 472 may be a diameter of the acoustic area 472 (e.g., with a circular acoustic area 472). In other embodiments, the acoustic spot size 468 may be the major axis of the acoustic area 472 (e.g., with an elliptical acoustic area 472). In yet other embodiments, the acoustic spot size 468 may be the largest dimension of the acoustic area 472 (e.g., with an irregular polygonal acoustic area 472).

In some embodiments, the final spot size 462 of the optical area 474 may be a diameter of the optical area 474 (e.g., with a circular optical area 474). In other embodiments, the final spot size 462 may be the major axis of the optical area 474 (e.g., with an elliptical optical area 474). In yet other embodiments, the final spot size 462 may be the largest dimension of the optical area 474 (e.g., with an irregular polygonal optical area 474).

The area in which the acoustic area 472 and the optical area overlap may be the active area 476. In some embodiments, the active area 476 may be the same as the optical area 474 (e.g., when the optical area 474 is smaller than and within the acoustic area 472). In other embodiments, the active area 476 may be the same as the acoustic area 472 (e.g., when the acoustic area 472 is smaller than and within the optical area 474). In yet other embodiments, the active area 476 may have other shapes, such as when at least a portion of the acoustic area 472 and at least a portion of the optical area 474 do not overlap one another. For example, a circular acoustic area 472 and a circular optical area 474 may partially overlap to form a lens shape, such as a vesica piscis. Movement of the optical area 474 and/or the acoustic area 472 relative to one another may allow the tailoring of the active area 476 to energize and promote cavitation in a specific (e.g., elongated) area.

Figure 9:
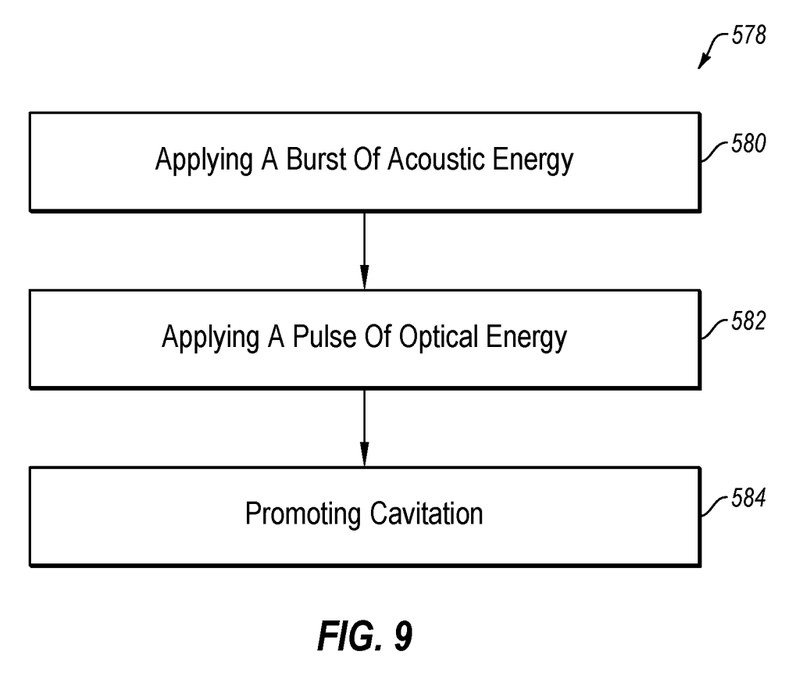
FIG. 9 is a flowchart illustrating an embodiment of a method of removing microvessels, according to at least one embodiment of the present disclosure.

FIG. 9 is a flowchart illustrating an embodiment of a method 578 of removing microvessels. In some embodiments, the method 578 may include applying a burst of acoustic energy at 580 to a target location. The acoustic energy may be provided by an acoustic energy source with any of the frequency, amplitude, duty cycle, or combinations thereof described herein. The acoustic energy may be focused to an acoustic spot size and/or acoustic area described herein.

The method 578 may further include applying a pulse of optical energy at 582 to the target location. The pulse of optical energy may be provided by an optical energy source with any wavelength, fluence, pulse duration, or combinations thereof described herein. In some embodiments, the optical energy may be focused to a final spot size and/or optical area described herein. In other embodiments, the optical energy may be focused to an initial spot size by one or more lenses, and the optical energy may then be focused to the final spot size by an eye.

In some embodiments, the application of the burst of acoustic energy may be insufficient to promote cavitation alone at the target location. In other embodiments, the application of the pulse of optical energy may be insufficient to promote cavitation alone at the target location. Overlapping at least a portion of the acoustic area and at least a portion of the optical area may result in promoting cavitation at 584 in an active area at the target location.

In some embodiments, the low power of the acoustic energy and the low power of the optical energy may produce cavitation only where the acoustic area and the optical area overlap. For example, the combination of the acoustic energy and the optical energy may produce an increase in temperature at the target location of no more than 1° Celsius. In other examples, the combination of the acoustic energy and the optical energy may produce an increase in temperature at the target location of no more than 2° Celsius. In yet other examples, the combination of the acoustic energy and the optical energy may produce an increase in temperature at the target location of no more than 3° Celsius.

The cavitation at the target location may cause the formation of bubbles, that mechanically induce physical and/or physiological effects on the microvessels at the target location. In some examples, the bubbles may have a diameter of no more than 1 µm. In other examples, the bubbles may have a diameter of no more than 2 µm. In yet other examples, the bubbles may have a diameter of no more than 3 µm.

One or more specific embodiments of the present disclosure are described herein. These described embodiments are examples of the presently disclosed techniques. Additionally, in an effort to provide a concise description of these embodiments, not all features of an actual embodiment may be described in the specification. It should be appreciated that in the development of any such actual implementation, as in any engineering or design project, numerous embodiment-specific decisions will be made to achieve the developers' specific goals, such as compliance with system-related and business-related constraints, which may vary from one embodiment to another. Moreover, it should be appreciated that such a development effort might be complex and time consuming, but would nevertheless be a routine undertaking of design, fabrication, and manufacture for those of ordinary skill having the benefit of this disclosure.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A system for promoting cavitation within microvessels in an eye, the system comprising:
    an acoustic energy source configured to focus an acoustic energy at a first target location, the acoustic energy having a pressure insufficient to cause cavitation in blood alone;
    an optical energy source configured to focus optical energy at a second target location, the optical energy having a fluence insufficient to cause cavitation in blood alone, the optical energy and the acoustic energy at least partially overlapping at the first target location, wherein the first target location and the second target location are different and wherein a rarefaction phase of the acoustic energy and a pulse of the optical energy source are synchronized at an overlapping region of the acoustic energy and the optical energy without the presence of extraneous nanoparticles or contrast agents.

2. The system of claim 1, the acoustic energy source being a therapeutic ultrasound transducer.

3. The system of claim 1, the optical energy source being a laser.

4. The system of claim 1, the optical energy source having an initial spot size of greater than 1.0 mm.

5. The system of claim 1, the acoustic energy having a maximum pressure less than 5.0 MPa.

6. The system of claim 1, the optical energy having a fluence less than 100 mJ/cm$^2$.

7. The system of claim 1, further comprising a stage configured to move the acoustic energy source and at least a portion of the optical energy source to move the target location.

8. A non-transient computer readable medium containing instructions for causing a computing device to perform a method of:
focusing an acoustic energy to a first target location, the acoustic energy having a pressure insufficient to cause cavitation in blood alone; and
focusing an optical energy to a second target location different from the first target location concurrently with the acoustic energy such that a rarefaction phase of the acoustic energy and a pulse of the optical energy are synchronized at an overlapping region of the acoustic energy and the optical energy without the presence of extraneous nanoparticles or contrast agents, the optical energy having a fluence insufficient to cause cavitation in blood alone, wherein a combination of the negative pressure of the acoustic energy during the rarefaction phase and the fluence of the optical energy pulse causes cavitation in blood.

9. The computer readable medium of claim 8, the pressure of the acoustic energy being less than 5.0 MPa.

10. The computer readable medium of claim 8, the fluence of the optical energy being less than 100 mJ/cm$^2$.

11. The computer readable medium of claim 8, the computer being in communication with an optical energy source and an acoustic energy source, the optical energy source being configured to provide the optical energy and the acoustic energy source being configured to provide the acoustic energy.

12. A system for promoting cavitation in microvessels in an eye, the system comprising:
an acoustic energy source configured to focus an acoustic energy at a first target location, the acoustic energy source having an opening therethrough and the acoustic energy having a pressure insufficient to cause cavitation in blood alone;
an optical energy source positioned to focus optical energy at a second target location different from the first target location through the opening in the acoustic energy source, the optical energy having a fluence insufficient to cause cavitation in blood alone, a pulse of the optical energy and a rarefaction phase of the acoustic energy being synchronized at an overlapping region of the acoustic energy and the optical energy without the presence of extraneous nanoparticles or contrast agents;
at least one defocusing lens positioned proximate the target location to defocus the optical energy toward the second target location;
a computing device in communication with the acoustic energy source and the optical energy source; and
one or more sensors configured to detect cavitation at the first target location, the one or more sensors being in communication with the computing device.

13. The system of claim 12, the acoustic energy and optical energy sharing a focal axis.

14. The system of claim 12, the optical energy having an optical area that is concentric with an acoustic area of the acoustic energy at the first target location.

15. The system of claim 14, the acoustic area having a diameter less than 4.0 mm at the first target location.

16. A method of removing microvessels, the method comprising:
applying a burst of acoustic energy focused at a first target location, the burst of said acoustic energy having a pressure below 5.0 MPa;
applying a pulse of optical energy focused at a second target location different from the first target location, the pulse of optical energy having a fluence less than 100 mJ/cm$^2$, at least a portion of the pulse being concurrent with a rarefaction phase of the burst and the optical energy having an optical area that is overlapping with an acoustic area of the acoustic energy at the first target location and wherein the acoustic energy source and the optical energy source are synchronized at an overlapping region of the acoustic energy and the optical energy such that the pulse is synchronized with the rarefaction phase without the presence of extraneous nanoparticles or contrast agents; and
promoting cavitation at the first target location.

17. The method of claim 16, the burst having a frequency between 500 kHz and 1 MHz.

18. The method of claim 16, the pulse having a wavelength between 400 nm and 2400 nm.

19. The method of claim 16, further comprising repeating the method for at least 1 minute.

20. The method of claim 16, wherein the pulse of optical energy is tuned to selectively target a tissue with a specific optical absorption.

* * * * *